United States Patent [19]

Jancis

[11] 4,018,808
[45] Apr. 19, 1977

[54] HYDRAZINO NICKEL THIO-BIS-PHENOLATES AND POLYOLEFINS STABILIZED THEREBY AGAINST THE EFFECTS OF HEAT AND LIGHT

[75] Inventor: Elmar Harry Jancis, Naugatuck, Conn.

[73] Assignee: Uniroyal, Inc., New York, N.Y.

[22] Filed: July 1, 1975

[21] Appl. No.: 592,142

Related U.S. Application Data

[62] Division of Ser. No. 439,801, Feb. 6, 1974, Pat. No. 3,925,308.

[52] U.S. Cl. .................... 260/439 R; 260/45.75 N; 260/242; 260/270 R; 260/326.8
[51] Int. Cl.² .......................................... C07F 15/04
[58] Field of Search ................ 260/439 R, 45.75 N

[56] References Cited

UNITED STATES PATENTS

| | | | |
|---|---|---|---|
| 3,215,717 | 11/1965 | Foster | 260/439 R |
| 3,218,294 | 11/1965 | Rodgers et al. | 260/439 R X |
| 3,636,022 | 1/1972 | Bright | 260/439 R |
| 3,636,023 | 1/1972 | Murray et al. | 260/439 R |
| 3,692,738 | 9/1972 | Mathis et al. | 260/45.75 N |
| 3,816,492 | 1/1974 | Stretanski et al. | 260/439 R |

*Primary Examiner*—Helen M. S. Sneed
*Attorney, Agent, or Firm*—Bruce F. Jacobs

[57] ABSTRACT

The disclosure relates to a new class of compounds useful in stabilizing organic materials against the effects of heat and light, such materials especially including polymers such as polyolefins. The new compounds are hydrazine complexes of nickel thio-bis-phenolates, where the thio-bis-phenol is of the formula,

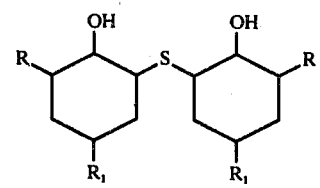

where R is selected from the group consisting of hydrogen, normal alkyl or normal alkenyl, and $R_1$ is selected from the group consisting of a normal, secondary, tertiary or cyclic alkyl group. The hydrazines used in making the complexes are of the formula

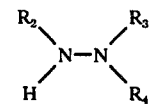

where $R_2$, $R_3$ and $R_4$ are independently chosen from the group hydrogen and primary, secondary and tertiary alkyl groups consisting of 1 to 8 carbon atoms and $R_3$ and $R_4$ may be joined together to form a heterocyclic structure.

The resulting nickel complexes have been found to function as superior stabilizers for organic polymers and for polyolefins in particular, and also to perform synergistically in combination with other stabilizers of the prior art.

5 Claims, No Drawings

HYDRAZINO NICKEL THIO-BIS-PHENOLATES AND POLYOLEFINS STABILIZED THEREBY AGAINST THE EFFECTS OF HEAT AND LIGHT

This is a division, of application Ser. No. 439,801, filed Feb. 6, 1974, now U.S. Pat. No. 3,925,308.

BACKGROUND OF THE INVENTION

1. Field of the Invention

This invention relates to a novel class of compounds useful in stabilizing organic materials against the effects of heat and light. The materials to be protected by these compounds include organic polymers such as polyolefins and more particularly, polyethylene and polypropylene, and the invention includes compositions containing such polymers and said stabilizers incorporated therein.

2. Description of the Prior Art

Metal salts of thio-bis-phenols have been known as rubber antioxidants for a long time (U.S. Pat. No. 2,310,449 — 1943). In particular, nickel salts have been found to be very effective (U.S. Pat. No. 2,380,299 — 1945). These salts have also been found useful as lubricating oil additives (U.S. Pat. No. 2,402,448 — 1946). Nickel salts of para-alkylphenol sulfides have furthermore found use in polypropylene (U.S. Pat. No. 2,971,940 — 1961), polyethylene (U.S. Pat. No. 2,971,941 — 1961) as well as in other polyolefins (U.S. Pat. No. 3,006,886 — 1961). Because of the ease of its preparation (U.S. Pat. No. 2,971,968 — 1961; U.S. Pat. No. 3,390,160 — 1968) — the para-tetramethylbutylphenol sulfide nickel salt has become the article of commerce. One of its advantages is that it is compatible with other additives that are commonly used in stabilizing polyolefins such as phenolics, thiodipropionates, phosphites, benzophenones and benzotriazoles (U.S. Pat. No. 3,006,885; 3,006,886; 3,074,910; 3,167,526; 3,481,897; 3,637,588).

Recently the butylamine complex of the nickel 2,2'-thio-bis(4-tetramethylbutylphenolate) has made great inroads on the market of the above named predecessor, mainly because of its increased activity (U.S. Pat. No. 3,215,717 — 1965). This compound too is compatible with the usual compounding ingredients used in polyolefins (U.S. Pat. No 3,218,294; 3,379,680; 3,481,897).

Most recently the alkanolamine complexes of nickel 2,2'-thio-bis(4-alkylphenolates) have been patented (U.S. Pat. No. 3,636,023 — 1972).

SUMMARY OF THE INVENTION

In accordance with this invention it has been discovered that a new class of compounds composed of hydrazine complexes of nickel 2,2'-thio-bis-(4-alkylphenols), or nickel 2,2'-thio-bis-(4,6-dialkylphenols), have superior activity as stabilizers against the effects of heat and light when incorporated in organic materials. These compounds are especially useful as additives to organic polymers especially polyolefins such as polyethylene and polypropylene.

An object of the present invention therefore is to provide a new class of compounds as well as specific members thereof especially useful as stabilizers of organic materials against heat and light.

A further object of the present invention is to provide a polymeric composition comprising a polyolefin stabilized against light and heat by the incorporation therewith of a compound of the present invention.

An additional object of the present invention is to provide a stabilizer which will function synergistically in combination with other stabilizers resulting in enhanced stability of polyolefins against heat and light.

PREFERRED EMBODIMENTS OF THE PRESENT INVENTION

The thio-bis-phenols mentioned have the formula

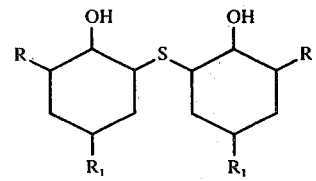

where R is hydrogen, n-alkyl or n-alkenyl. $R_1$ is an alkyl group of any description. It can be normal, secondary, tertiary, cyclic and may contain unsaturation.

The preparation of thio-bis-phenols is fully described in the literature (prior art cited), more particularly, U.S. Pat. Nos. 2,971,940; 2,971,968 and 3,006,886.

R is usually hydrogen or methyl and $R_1$ a methyl, tertiary butyl or tertiary octyl group.

Representative 2,2'-thio-bis-phenols include
2,2'-thio-bis-(4-ethylphenol)
2,2'-thio-bis-(4-tert-butylphenol)
2,2'-thio-bis-(4-tert-amylphenol)
2,2'-thio-bis-(4'-iso-propylphenol)
2,2'-thio-bis-(4'-tert-octylphenol)
2,2'-thio-bis-(4'-nonylphenol)
2,2'-thio-bis-(4'-dodecylphenol)
2,2'-thio-bis-(4'-tert-butyl-o-cresol)
2,2'-thio-bis-(4'-tert-octyl-o-cresol)
2,2'-thio-bis-(4'-tert-octyl-6-allylphenol)
2,2'-thio-bis-(4'-tert-octyl-6-n-propylphenol)

The hydrazines used in making the complexes have the formula

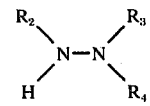

where $R_2$, $R_3$, and $R_4$ are independently chosen from the group consisting of hydrogen and primary, secondary and tertiary alkyl groups consisting of 1 to 8 carbon atoms and $R_3$ and $R_4$ may be joined together with the nitrogen to form a heterocyclic structure of the formula

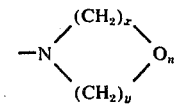

where $x$ is 1 to 3, $y$ is 1 to 3 and $n$ is zero or one. Examples of hydrazines having this heterocyclic structure are N-aminopyrrolidine, N-aminopiperidine and N-aminomorpholine.

The hydrazines used to complex the nickel thio-bis-phenolates can be hydrazine itself, mono, di- and tri-substituted hydrazines. The substituents are preferably alkyl groups. Two substituents could be joined together to form a cyclic structure. Thus N-aminomorpholine and N-aminopiperidine are very useful hydrazines for this invention.

Arylhydrazines, heterocyclically substituted hydrazine and hydroxy ethyl hydrazines have been used to make the nickel complexes, but gave products inferior to simple alkylhydrazine complexes.

The hydrazines useful in preparing the nickel complexes of the invention are as follows:
hydrazine
1,1-dimethylhydrazine
1,2-dimethylhydrazine
1,1,2-trimethylhydrazine
1,1-diethylhydrazine
1,2-diethylhydrazine
1,1-dimethyl-2-ethylhydrazine
1,1-dimethyl-2-n-propylhydrazine
1,1-dimethyl-2-isopropylhydrazine
1,1-dimethyl-2-n-butylhydrazine
1,1-dimethyl-2-sec-butylhydrazine
1,1-dimethyl-2-amylhydrazine
1,1-di-n-propylhydrazine
1,1-di-isopropylhydrazine
1,1-di-n-butylhydrazine
1,1-di-sec-butylhydrazine
1,1-di-amylhydrazine
methylhydrazine
ethylhydrazine
iso-propylhydrazine
n-propylhydrazine
n-butylhydrazine
sec-butylhydrazine
n-amylhydrazine
sec-amylhydrazine
tert-amylhydrazine
hexylhydrazine
cyclopentylhydrazine
cyclohexylhydrazine
N-aminopyrrolidine
N-amino-piperidine
N-amino-morpholine, etc.

The hydrazines of choice are hydrazine itself and 1,1-dimethylhydrazine.

The use of hydrazines to complex the nickel thio-bis-phenolates is the key to the invention. Ordinary amines have already been used to form analogous complexes. We found that compounds of this invention have superior activity to previously described compounds, e.g. in polypropylene fiber the dimethylhydrazine complex was superior to the corresponding butylamine complex (marketed as Cyasorb 1084).

The complexes of this invention are readily prepared by the methods described in the aforementioned prior art on amine complexes of nickel thio-bis-phenolates and as described in the examples below.

The compounds of this invention are useful for stabilizing organic materials against the effects of heat and light. They are particularly effective in stabilizing poly-α-olefins such as polyethylene and polypropylene. The nickel complexes obtained are compatible with all the other ingredients used to compound commercial resins such as phenolics, thioesters, lubricants, pigments and other light stabilizers. A synergistic effect is actually noted in using mixtures of hydrazino nickel compounds with benzotriazole or benzophenone type light stabilizers of the type commercially available.

The following specific Examples illustrate the practice of the invention.

EXAMPLE I

Preparation of dimethyl hydrazine nickel complex of 2,2'-thio-bis-(p-tert-octylphenol) (1:1 salt)

To a solution of 47 parts nickel 2(2'-hydroxy-5'-tert-octylphenyl thio)-4-tert-octylphenolate in 400 ml. chloroform was added 15 ml. 1,1-dimethylhydrazine followed by 15g. nickel acetate tetrahydrate in 200 ml. water. After stirring three hours, the layers were separated. The chloroform layer was washed with water. The chloroform was filtered through cottom and was then evaporated. The green residue was triturated with hot ethanol whereupon the nickel salt crystallized. The salt was filtered and dried. The product melted at 260°–267° C and contained 10.5% nickel by analysis (% Ni calculated — 11.0).

Other hydrazine complexes were prepared in an analogous fashion.

Hydrazine complex M.p. 255°–263° C. % Ni 10.3
Methylhydrazine complex M.p. 280°–300° C. % Ni 12.2
Dibutylhydrazine complex M.p. 238°–245° C. % Ni 9.5
Aminomorpholine complex M.p. 245°–265° C. % Ni 10.4
Phenylhydrazine complex M.p. 127°–150° C. % Ni 9.9
Aminopiperidine complex M.p. 260°–278° C. % Ni 11.5

EXAMPLE II

Nickel complex preparation from other thio-bis-phenols

To 18g. of 2,2'-thio-bis(4-tert-butyl-o-cresol) in 150 ml. chloroform was added 10 ml. 1,1-dimethylhydrazine followed by a solution of 15 g. nickel acetate tetrahydrate in 100 ml. water. The mixture was stirred 2 hours, another 5 ml. of 1,1-dimethylhydrazine was added, and stirred another hour. The layers was separated; the chloroform layer was washed with water and filtered through cotton. The residue after chloroform evaporation was recrystallized from methanol/water.

The product melted at 255°–270° C and contained 12.6% nickel.

In an analogous fashion were prepared the dimethylhydrazino nickel complexes from
2,2'-thio-bis(4-tert-butylphenol) M.p. over 300° C, 14.6% Ni
2,2'-thio-bis(4-nonylphenol) M.p. 195°–202° C, 10.1% Ni
2,2'-thio-bis(6-allyl-4-tert-octylphenol) M.p. 165°–183° C, 8.6% Ni
2,2'-thio-bis(6-n-propyl-4-tert-octylphenol) M.p. 88°–102° C, 7.3% Ni

EXAMPLE III

This Example is designed to show the superiority of the material made in Example I to the commercial butylamine complex (Test A. below)

Polypropylene fibers were drawn from Profax 6501 resin containing 0.2% distearylthiodipropionate, 0.1% Irganox 1010 (a phenolic stabilizer), 0.05% dibutyl p-cresol, 0.2% calcium stearate and 0.5% light stabilizer as follows:
  A. 0.5% butylamine complex of nickel 2,2'-thio-bis(4-tert-octylphenolate)
  B. 0.5% dimethylhydrazine complex (Example I)
  C. 0.25% 4-octyloxy-2-hydroxybenzophenone and 0.25% butylamine complex A D. 0.25% 4-octyloxy-2-hydroxybenzophenone and 0.25 dimethylhydrazine complex (Example I)
E. 0.5% 4-octyloxy-2-hydroxybenzophenone
F. 0.5% hydrazine complex (Example I)
G. 0.25% hydrazine complex (Example I) and 0.25% 4-octyloxy-2-hydroxybenzophenone
H. No light stabilizer.

B, D, F and G are the Examples of the invention.

The multifilament yarn (ca. 300 denier) was mounted and exposed in a fluorescent Sunlight/Blacklight unit for 8 days. Tensile strengths and % elongations were taken before and after aging.

|   | % Initial properties retained | |
|---|---|---|
|   | Tensile | Elongation |
| A | 66 | 21 |
| B | 79 | 37 |
| C | 79 | 38 |
| D | 97 | 41 |
| E | 72 | 49 |
| F | 54 | 27 |
| G | 77 | 43 |
| H | 0 | 0 |

Note the synergistic effect with 4-octyloxy-2-hydroxybenzophenone in preserving the tensile strength.

EXAMPLE IV

This Example is designed to show the superiority of the compounds of this invention in polypropylene film compared to an ethanolamine complex compound of U.S. Pat. No. 3,636,023 (Test C).

Ten (10) mil polypropylene films were compression molded from Profax 6501 resin containing 0.4 parts dilauryl thiodipropionate and 0.2 parts nickel stabilizer.

They were exposed in an oven at 300° F and in Fluorescent Sunlight Blacklight unit FSLBL. The time to embrittlement was noted.

|   | Days to Embrittlement | |
|---|---|---|
|   | OVEN | FSLBL |
| A. Hydrazine complex (Example I) | 42 | 36 |
| B. Dimethylhydrazine complex (Example I) | 44 | 23 |
| C. Ethanolamine complex of nickel 2,2'-thio-bis(4-tert-octylphenolate) | 36 | 14 |
| D. No nickel | 23 | 13 |

EXAMPLE V

This Example is designed to show the general utility of hydrazino-nickel-bis phenolates in polypropylene.

Ten (10) mil polypropylene films were compression molded from Profax 6501 resin containing 0.4 parts dilauryl thiodipropionate and 0.5 parts nickel stabilizer.

They were exposed in an oven at 300° F and in a Fluorescent Sunlight Blacklight unit. The days to embrittlement were noted.

| Nickel complex | Days to Embrittlement | |
|---|---|---|
|   | OVEN | FSLBL |
| A. None | 23 | 13 |
| B. Dimethylhydrazine complex (Example I) | 31 | 50 |
| C. Hydrazine complex (Ex.I) | 35 | 50 |
| D. Methylhydrazine complex (Ex.I) | 35 | 49 |
| E. Dibutylhydrazine complex (Ex.I) | 46 | 37 |
| F. Aminomorpholine complex (Ex.I) | 41 | 46 |
| G. Aminopiperidine complex (Ex.I) | 35 | 53 |
| H. Phenylhydrazine complex (Ex.I) | 35 | 34 |
| I. Dimethylhydrazino nickel complex of 2,2'-thio-bis(4-tert-butyl-o-cresol) (Ex. II) | 26 | 42 |
| J. Dimethylhydrazino nickel complex of 2,2'-thio-bis-(4-tert-)butyl-phenol) (Ex. II) | 15 | 62 |

EXAMPLE VI

This Example is designed to show the usefulness of the compounds of this invention in polyethylene.

Ten (10) mil films were compression molded from Profax A60 – 008 polyethylene resin containing 0.05% distearyl thiodipropionate and 0.2 parts nickel stabilizer. They were exposed in a Fluorescent Sunlight Blacklight unit and the number of days to embrittlement noted.

|   | Days to Embrittlement |
|---|---|
| A. No nickel | 13 |
| B. Dimethylhydrazine complex (Ex.I) | 51 |
| C. Hydrazine complex (Example I) | 51 |

EXAMPLE VII

This Example illustrates the superiority of the compounds of this invention in polypropylene film.

Some films prepared in the same fashion as in Example IV were also exposed in a xenon arc Fadeometer. Results show hours to embrittlement.

|   | Hours to Embrittlement |
|---|---|
| No nickel salt | 239 |
| Butylamine complex of nickel 2,2'-thio-bis-(4-tetramethylbutylphenolate) | 500 |
| Hydrazine complex (Example I) | 507 |
| Dimethylhydrazine complex (Ex. I) | 555 |

When compounded at the 0.1 part level with 0.1 parts 4-octyloxy-2-hydroxybenzophenone the hours to embrittlement in the xenon arc Fadeometer are:

|   | Hours to Embrittlement |
|---|---|
| Butylamine complex (as above) | 699 |
| Hydrazine complex (Example I) | 744 |
| Dimethylhydrazine complex (Ex. I) | 1075 |

EXAMPLE VIII

This example illustrates the improved processing safety of the compounds of this invention in polypropylene over the commercial butylamine complex as measured by the melt index.

| Melt Index Measurement of Extrudates Melt Index ASTM 1238/65T (Grams/10 Minutes) | | | | | | |
|---|---|---|---|---|---|---|
| | Unextruded | 450° | 475° | 500° | 525° | 550° F. |
| Dimethyl-hydrazine complex (Ex. I) | 4.4 | 5.4 | 5.7 | 6.2 | 6.8 | 7.1 |
| Butylamine complex (Example III A) | 5.0 | 5.8 | 7.2 | 7.2 | 8.7 | 8.5 |

The above Examples clearly illustrate the utility and effectiveness of the nickel complexes of the invention in preserving the physical characteristics of polyolefins against exposure to heat and light, either as the sole stabilizing agent or synergistically in combination with others. In Example III, tests run against the nickel butylamine complex of the prior art show that all of the nickel hydrazine complexes except the hydrazine complex gave substantially higher preservation of tensile strength and elongation. The hydrazine complex while less effective with respect to tensile strength, gave a better elongation result. Significantly, the hydrazine complex with a hydroxybenzophenone stabilizer gave a clear picture of synergy.

In Example IV comparison with an ethanolamine complex of U.S. Pat. No. 3,636,023 in polypropylene film demonstrated clear superiority of the nickel hydrazine and dimethylhydrazine complexes of the invention.

The relative effectiveness of the nickel complexes of the invention are demonstrated in the oven and fluorescent blacklight sunlight tests of Example V.

As shown in Example VI, the nickel complexes of the invention are highly effective when compounded with polyethylene.

In Example VII comparison with the butylamine complex of nickel 2,2′-thio-bis(4-tetramethylbutyl-phenolate) demonstrated superiority of the nickel hydrazine and dimethylhydrazine complexes when compared alone and combined with 4-octyloxy-2-hydroxybenzophenone. Although some synergistic activity appears to exist with the butylamine complex combinations, it is obviously much greater in the combination with the nickel complexes of this invention.

In general, stabilizers of the present invention are effective over a broad range of concentrations, namely about 0.05% to about 5%. The specific proportion to be used will be within the skill of the worker in the art and will depend on the nature of the polymer, its intended use, and the conditions to which it will be exposed.

The stabilizers are incorporated in the polymeric material in a manner well known to the art as by intimately mixing with the polymer prior to extrusion by milling or suspension in the material to be shaped.

I claim:

1. Hydrazino nickel thio-bis-phenolates which are the hydrazine complexes which of nickel thio-bis-phenolates, where the thio-bis-phenol is of the formula

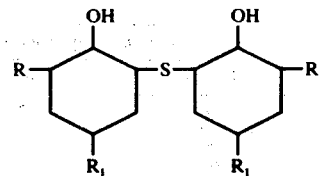

where R is selected from the group consisting of hydrogen, normal alkyl or normal alkenyl, and $R_1$ is selected from the group consisting of normal, secondary, tertiary and cyclic alkyl groups, and the hydrazine is of the formula

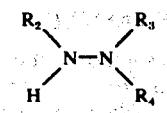

where $R_2$, $R_3$ and $R_4$ are independently chosen from the group consisting of hydrogen and primary, secondary and tertiary alkyl groups consisting of 1 to 8 carbon atoms.

2. The hydrazino nickel thio-bis-phenolate of claim 1 wherein the thio-bis-phenolate is 2,2′-thio-bis(4-tert-octylphenol) and the hydrazine is dimethylhydrazine.

3. The hydrazino nickel thio-bis-phenolate of claim 1 wherein the thio-bis-phenolate is 2,2′-thio-bis(4-tert-octylphenol) and the hydrazine is hydrazine itself.

4. The hydrazino nickel thio-bis-phenolate of claim 1 wherein the thio-bis-phenolate is 2,2′-thio-bis(4-tert-butyl-octylcresol) and the hydrazine is dimethylhydrazine.

5. The hydrazino nickel thio-bis-phenolate of claim 1 wherein the thio-bis-phenolate is 2,2′-thio-bis(4-tert-butylphenol) and the hydrazine is dimethyl hydrazine.

* * * * *